United States Patent
Savord et al.

(10) Patent No.: US 11,097,312 B2
(45) Date of Patent: Aug. 24, 2021

(54) CAPACITIVE MICROMACHINED ULTRASONIC TRANSDUCERS WITH INCREASED LIFETIME

(71) Applicant: KONINKLIJKE PHILIPS N.V., Eindhoven (NL)

(72) Inventors: Bernard Joseph Savord, Andover, MA (US); Richard Edward Davidsen, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 680 days.

(21) Appl. No.: 15/751,207

(22) PCT Filed: Aug. 4, 2016

(86) PCT No.: PCT/EP2016/068676
§ 371 (c)(1),
(2) Date: Feb. 8, 2018

(87) PCT Pub. No.: WO2017/025438
PCT Pub. Date: Feb. 16, 2017

(65) Prior Publication Data
US 2018/0229268 A1    Aug. 16, 2018

Related U.S. Application Data

(60) Provisional application No. 62/203,531, filed on Aug. 11, 2015.

(30) Foreign Application Priority Data

Sep. 1, 2015  (EP) ..................................... 15183228

(51) Int. Cl.
| | | |
|---|---|---|
| B06B 1/02 | (2006.01) | |
| A61B 8/00 | (2006.01) | |
| G01N 29/24 | (2006.01) | |

(52) U.S. Cl.
CPC .......... *B06B 1/0292* (2013.01); *A61B 8/4483* (2013.01); *G01N 29/2406* (2013.01); *B06B 2201/76* (2013.01)

(58) Field of Classification Search
CPC combination set(s) only.
See application file for complete search history.

(56) References Cited

U.S. PATENT DOCUMENTS

| | | |
|---|---|---|
| 5,997,479 A | 12/1999 | Savord et al. |
| 6,283,919 B1 | 9/2001 | Roundhill et al. |

(Continued)

*Primary Examiner* — Isam A Alsomiri
*Assistant Examiner* — Amie M Ndure

(57) ABSTRACT

An array of CMUT cells (10) has a DC bias voltage (VB) coupled to the top electrodes of the cells to bias the electrode to a desired collapsed or partially collapsed state. Fuses (200) are coupled in series with the bottom electrodes (22) of the cells which will open and isolate an individual cell from the other still-functional cells of the array in the event of a failure of the individual cell. In a preferred embodiment the cells are coupled to control integrated circuitry such as microbeamformer circuitry and the fuses are formed of semiconductor materials with the integrated circuitry, thereby leaving the MUT surface area available for high density MUT fabrication. Damage to the integrated circuitry due to short-circuiting of the DC bias current through a failed cell is prevented.

17 Claims, 6 Drawing Sheets

(56) References Cited

U.S. PATENT DOCUMENTS

| | | | |
|---|---|---|---|
| 6,328,697 B1 | 12/2001 | Fraser | |
| 6,443,896 B1 | 9/2002 | Detmer | |
| 6,458,083 B1 | 10/2002 | Jago et al. | |
| 6,530,885 B1 | 3/2003 | Entrekin et al. | |
| 6,623,432 B2 | 9/2003 | Powers et al. | |
| 7,293,462 B2 | 11/2007 | Lee et al. | |
| 8,085,964 B2* | 12/2011 | Cohen | H04R 1/20 381/334 |
| 8,126,163 B2* | 2/2012 | Cohen | H04R 3/04 381/98 |
| 8,157,740 B2* | 4/2012 | Adachi | B06B 1/0292 600/463 |
| 8,431,420 B2* | 4/2013 | Kobayashi | B06B 1/0292 438/16 |
| 8,457,338 B2* | 6/2013 | Cohen | H04R 1/403 381/334 |
| 8,755,556 B2* | 6/2014 | Cohen | H04R 31/00 381/398 |
| 8,780,673 B2* | 7/2014 | Cohen | H02N 13/00 367/140 |
| 9,233,396 B2* | 1/2016 | Jeong | B06B 1/0629 |
| 9,351,706 B2* | 5/2016 | Rothberg | A61B 8/4477 |
| 9,391,541 B2* | 7/2016 | Cohen | H02N 1/002 |
| 9,425,708 B2* | 8/2016 | Haber | H02N 1/006 |
| 9,592,030 B2* | 3/2017 | Rothberg | A61B 8/4483 |
| 9,654,890 B2* | 5/2017 | Haber | H04R 1/005 |
| 9,880,533 B2* | 1/2018 | Lewin | G05B 15/02 |
| 2005/0200241 A1* | 9/2005 | Degertekin | B06B 1/0292 310/334 |
| 2006/0116106 A1* | 6/2006 | Turner | H01J 37/32174 455/410 |
| 2006/0145059 A1* | 7/2006 | Lee | H04R 23/00 250/214 R |
| 2010/0168576 A1* | 7/2010 | Poland | A61B 8/4427 600/443 |
| 2011/0140212 A1 | 6/2011 | Itoh et al. | |
| 2011/0163630 A1 | 7/2011 | Klootwijk et al. | |
| 2012/0058587 A1* | 3/2012 | Chang | B81C 1/00476 438/53 |
| 2013/0088118 A1* | 4/2013 | Ho | B06B 1/0292 310/300 |
| 2013/0169110 A1 | 7/2013 | Jeong et al. | |
| 2013/0320940 A1* | 12/2013 | Dimitrovski | G05F 1/32 323/249 |
| 2014/0070669 A1* | 3/2014 | Jeong | B06B 1/0292 310/336 |
| 2015/0016221 A1* | 1/2015 | Takeuchi | B06B 1/0292 367/87 |
| 2015/0016227 A1 | 1/2015 | Brock-Fisher | |
| 2015/0103430 A1* | 4/2015 | Gadbois | G11B 5/4853 360/59 |
| 2016/0164458 A1* | 6/2016 | Nguyen | G01C 19/5698 331/155 |
| 2016/0310992 A1* | 10/2016 | Van Rens | A61B 8/4444 |
| 2017/0047893 A1* | 2/2017 | Nguyen | H03H 9/171 |

* cited by examiner

CAPACITIVE MICROMACHINED ULTRASONIC TRANSDUCERS WITH INCREASED LIFETIME

This application is the U.S. National Phase application under 35 U.S.C. § 371 of International Application No. PCT/EP2016/068676, filed on Aug. 4, 2016, which claims the benefit of Provisional Application Ser. No. 62/203,531, filed Aug. 11, 2015 and EP Application Serial No. 15183228.4 filed Sep. 1, 2015. These applications are hereby incorporated by reference herein.

FIELD OF THE INVENTION

This invention relates to medical diagnostic ultrasonic imaging and, in particular, to ultrasonic transducer probes which use capacitive micromachined ultrasonic transducers (CMUTs).

BACKGROUND OF THE INVENTION

Traditionally, ultrasonic transducers are formed of piezoelectric ceramic materials such as PZT or of piezoelectric polymers such as PVDF. Recently it has been shown that transducers can be made by semiconductor processes. Such transducers are formed of tiny semiconductor cells in which a vibrating membrane generates and receives the ultrasonic energy and are referred to as micromachined ultrasonic transducers (MUTs.) Two such transducer types are those which utilize a piezoelectric material on the membrane called piezoelectric micromachined ultrasonic transducers (PMUTs) and those which utilize a capacitive effect between a conductive membrane and another electrode called capacitive micromachined ultrasonic transducers (CMUTs.) Individual transducer elements may be formed of dozens or hundreds of such MUT cells operating in unison. Since these cells are very small, each MUT cell only produces or responds to a small amount of acoustic energy. Two approaches are commonly used to increase the acoustic efficiency of MUT devices. One is to bias the cells with a DC bias voltage which, in the case of CMUTs, brings the vibrating membrane into close proximity to the opposing electrode, increasing the sensitivity of the devices. Another is to form an array of cells which are very close to each other, maximizing the density of the cells on their substrate and providing a large number of cells which are operated in unison as a single transducer element. The high density fabrication of the cells also improves their grating lobe characteristics and reduces clutter in the resultant ultrasonic images.

A transducer array or even an individual element can thus comprise hundreds or thousands of individual MUT cells which are biased by the DC bias voltage. While such an architecture has numerous performance advantages as described above, a problem arises in that the failure of a single MUT cell can render a vast number of cells inoperative. It is possible for a single cell to fail by collapse of the membrane with its high DC bias voltage onto the opposing electrode. This shorts out not only the failed cell, but also all of the hundreds or thousands of other cells with which it is commonly biased. While the failure of a single cell by itself may not appreciably affect the performance of the transducer probe, the shorting out of a large number of other cells can render the entire transducer probe inoperative. One approach to prevent this problem is described in U.S. Pat. No. 7,293,462 (Lee et al.) The approach of Lee et al. is to form a fuse at the end of a row or column of interconnected MUT cells which will open when one cell in the row or column shorts out. This will remove the row or column of cells from operation in the transducer, allowing the other cells in the transducer to remain functioning. There are several drawbacks to this approach, however. One is that each row or column of interconnected cells must be separately biased, increasing the complexity of providing bias voltages to all of the cells in the probe. Another is that a fuse occupies a relatively large area on the MUT substrate, decreasing the area on the substrate available for MUT cells and hence the sensitivity of the transducers. Yet another is that a plurality of cells are removed from operation in the probe, the failed cell as well as the others to which it is connected, which also degrades the performance of the ultrasound probe. It would be desirable to be able to remove only a failed cell from operation, allowing the other fully functioning cells to remain in operation. U.S. Pat. No. 7,293,462 suggests providing a plurality of spokes interconnecting top electrode of each MUT cell to its neighbors. The spoke is designed to melt when the current flow there through is great enough. The drawback of this solution is that each MUT cell requires a plurality of fuses, which may complicate the array design and require additional space. Further, this solution also requires all fuses to be activated at once, if at least one spoke of U.S. Pat. No. 7,293,462 does not melt all interconnected electrodes will be shorted.

Accordingly it is an objective of the present invention to increase the lifetime of a MUT probe by removing only a failed MUT cell from operation, allowing the remaining fully functional cells to remain in operation. It is a further objective to do so in a way which does not utilize substrate area that could otherwise be used for MUT fabrication, thereby maintaining the MUT density of the MUT array and hence its sensitivity.

SUMMARY OF THE INVENTION

In accordance with the principles of the present invention, an ultrasonic transducer MUT cell array has one fuse for each individual cell of the array, which isolates only a failed cell from the remaining cells in the array, which remain fully operational. Each MUT cell has a membrane comprising a top electrode and a bottom electrode coupled to the substrate, wherein one of the top or bottom electrodes is a common electrode arranged to be coupled to a common reference potential (reference voltage), while another electrode is a signal electrode arranged to be coupled to an a.c. drive signal; and wherein each MUT cell further comprises one fuse coupled to the MUT signal electrode, the fuse operating to open in the event of an overcurrent condition of the MUT cell to isolate the MUT cell from the other MUT cells of the array.

The advantage of this solution is that placing the fuse on the signal side by coupling it to the a.c. signal bearing electrode allows a quick and efficient deactivation of the failed cell by keeping the density of the MUT array maximized. In addition to this, an operation of other cells in array sharing the common potential is not affected by the failed cell.

In another embodiment, the common electrode is arranged to be coupled to a ground potential, while the signal electrode is arranged to be coupled to both a DC reference potential and the a.c. drive signal.

The ground electrode of each failed cell is coupled to the ground potential, therefore, minimizing its influence on performance of the rest of the MUT cells in the array.

In another embodiment the ultrasonic transducer MUT cell array can comprise a DC bias voltage supply arranged to provide either a reference potential (either common potential with respect to the common electrode or a D.C. reference potential with respect to the signal electrode).

In a preferred implementation the fuses are formed on an application-specific integrated circuit (ASIC) which controls the individual MUTs. A fuse for a MUT can be formed by narrowing an integrated circuit channel conducting current to or from the MUT cell such that an overcurrent condition will cause either heat to open the channel or the channel to open through electro-migration. By forming the fuses on a high density ASIC, no area of the MUT substrate which could otherwise be used for MUT fabrication is used for the fuses, maintaining a high cell density on the MUT substrate for good acoustic performance. The control ASIC may be formed as a separate integrated circuit chip such as one used for microbeamforming which is bonded to the MUT substrate by known techniques, or the ASIC may be formed on the substrate used for MUT fabrication.

DETAILED DESCRIPTION OF THE EMBODIMENTS

Figure 1:
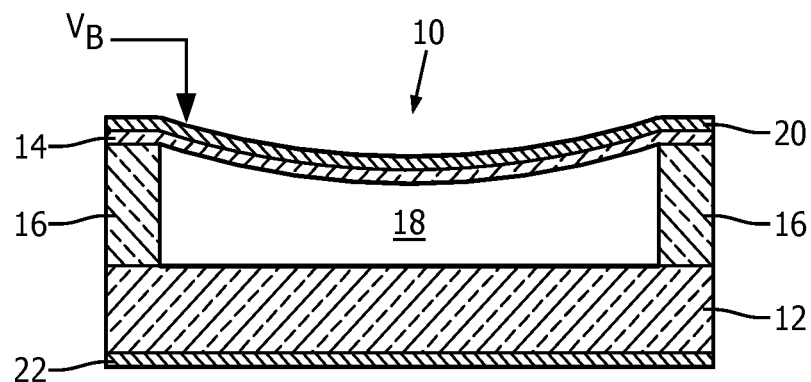
FIG. 1 is a cross-sectional view of a typical suspended-membrane CMUT transducer cell.

CMUTs were initially constructed to operate in what is now known as a suspended or "uncollapsed" mode. Referring to FIG. 1, a typical uncollapsed CMUT transducer cell 10 is shown in cross-section. The CMUT transducer cell 10 is fabricated along with a plurality of similar adjacent cells on a substrate 12 such as silicon. A diaphragm or membrane 14 which may be made of silicon nitride is supported above the substrate by an insulating support 16 which may be made of silicon oxide or silicon nitride. The cavity 18 between the membrane and the substrate may be air or gas-filled or wholly or partially evacuated. A conductive film or layer 20 such as gold forms an electrode on the diaphragm, and a similar film or layer 22 forms an electrode on the substrate. These two electrodes, separated by the dielectric cavity 18, form a capacitance. When an acoustic signal causes the membrane 14 to vibrate the variation in the capacitance can be detected, thereby transducing the acoustic wave into a corresponding electrical signal. Conversely, an a.c. signal applied across the electrodes 20,22 will modulate the capacitance, causing the membrane to move and thereby transmit an acoustic signal. A DC bias voltage $V_B$ from a DC bias voltage supply 140 is also applied across the electrodes, drawing the membrane and its top electrode 20 into close proximity with the floor of the cavity of the cell to increase sensitivity.

Figure 2:
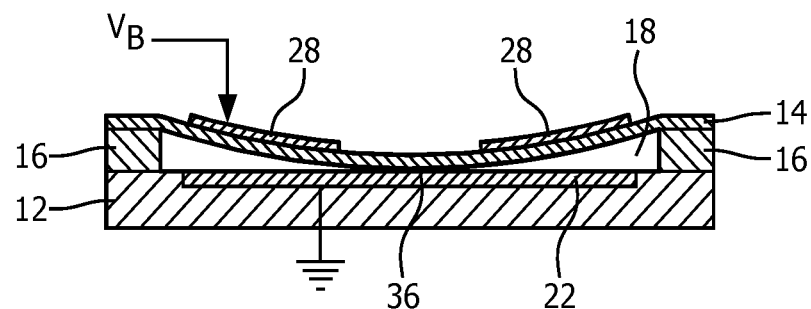
FIG. 2 is a cross-sectional view of a CMUT cell being operated in the collapsed mode.

FIG. 2 is a schematic cross-section of a CMUT cell which is operated in the collapsed mode. The CMUT cell includes a substrate layer 12 such as silicon, a substrate electrode 22, a membrane layer 14, and a membrane electrode ring 28. In this example, the electrode 22 is circularly configured and embedded in the substrate layer 12. In addition, the membrane layer 14 is fixed relative to the top face of the substrate layer 12 and configured/dimensioned so as to define a spherical or cylindrical cavity 18 between the membrane layer 14 and the substrate layer 12. The cell and its cavity 18 may define alternative geometries. For example, cavity 18 could define a rectangular and/or square cross-section, a hexagonal cross-section, an elliptical cross-section, or an irregular cross-section.

The bottom (substrate) electrode 22 is typically insulated on its cavity-facing surface with an additional layer (not pictured). A preferred insulating layer is an oxide-nitride-oxide (ONO) dielectric layer formed above the substrate electrode and below the membrane electrode. The ONO-dielectric layer advantageously reduced charge accumulation on the electrodes which leads to device instability and drift and reduction in acoustic output pressure. The fabrication of ONO-dielectric layers on a CMUT is discussed in detail in European patent application no. 08305553.3 by Klootwijk et al., filed Sep. 16, 2008 and entitled "Capacitive micromachined ultrasound transducer." Use of the ONO-dielectric layer is desirable with collapsed mode CMUT, which are more susceptible to charge retention than are uncollapsed device. The disclosed components may be fabricated from CMOS compatible materials, e.g., Al, Ti, nitrides (e.g., silicon nitride), oxides (various grades), tetra ethyl oxysilane (TEOS), poly-silicon and the like. In a CMOS fab, for example, the oxide and nitride layers may be formed by chemical vapor deposition and the metallization (electrode) layer put down by a sputtering process. Suitable CMOS processes are LPCVD and PECVD, the latter having a relatively low operating temperature of less than 400° C.

Exemplary techniques for producing the disclosed cavity 18 involve defining the cavity in an initial portion of the membrane layer 14 before adding a top face of the membrane layer 14. Other fabrication details may be found in U.S. Pat. No. 6,328,697 (Fraser). In the exemplary embodiment depicted in FIG. 2, the diameter of the cylindrical cavity 18 is larger than the diameter of the circularly configured electrode plate 22. Electrode ring 28 may have the same outer diameter as the circularly configured electrode plate 22, although such conformance is not required. Thus, in an exemplary embodiment of the present invention, the electrode ring 28 is fixed relative to the top face of the membrane layer 14 so as to align with the electrode plate 22 below.

In FIG. 2 the CMUT cell membrane layer is biased to a collapsed state, in which the membrane 14 is in contact with the floor of the cavity 18. This is accomplished by applying a DC bias voltage to the two electrodes as indicated by voltage $V_B$ applied to the electrode ring 28 and a reference potential (ground) applied to the substrate electrode 22. In a preferred implementation of a CMUT cell of the present invention, the bottom electrode is not grounded but coupled to a DC reference potential and the a.c. drive signal for the cell (as well as received signals) are applied to and received at the bottom electrode. While the electrode ring 28 could also be formed as a continuous disk without the hole in the center, FIG. 2 illustrates why this is not necessary. When the membrane 14 is biased to its precollapsed state as shown in this drawing, the center of the membrane is in contact with the floor of the cavity 18. As such, the center of the membrane 14 does not move during operation of the CMUT. Rather, it is the peripheral area of the membrane 14 which moves, that which is above the remaining open void of the cavity 18 and below the ring electrode. By forming the membrane electrode 28 as a ring, the charge of the upper plate of the capacitance of the device is located above the area of the CMUT which exhibits the motion and capacitive variation when the CMUT is operating as a transducer. Thus, the coupling coefficient of the CMUT transducer is improved.

Figure 3:
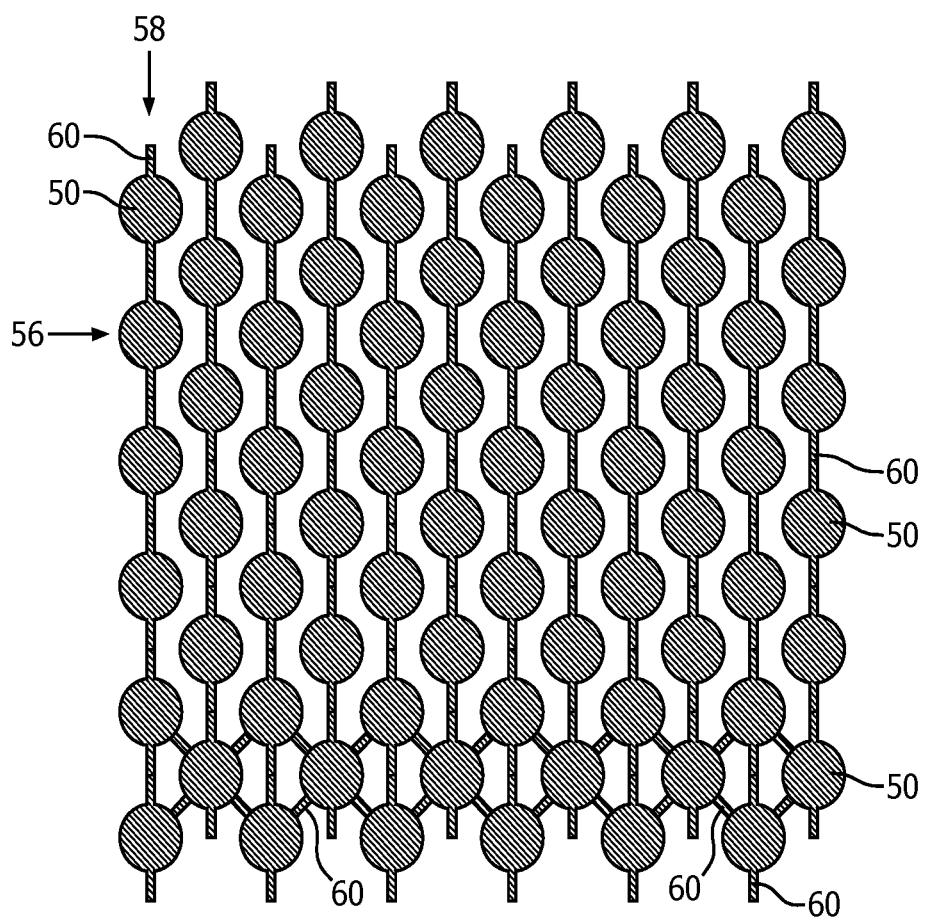
FIG. 3 is a plan view of a MUT array of the present invention with the rows and columns of the cells interconnected with a common biasing interconnect.

FIG. 3 is a top plan view of a two dimensional array of circular CMUT cells 50. The array is configured in a pattern of symmetrically aligned rows 56 and columns 58 of CMUT cells. The columns have a staggered alignment which allows the cells to be fabricated very close to each other to provide a high density array of cells. The rows and columns of cells 50 are overlaid and interconnected with an electrically conductive interconnect layer 60, which forms the conductive layer 20 on the cell membranes and also electrically couples them together. While only the bottom row is seen to be interconnected across the columns of cells in the drawing, in a constructed implementation each row is so connected such that each cell is connected to its six surrounding cells. This interconnect matrix uniformly distributes the common potential (defined either by applied bias voltage $V_B$ or ground potential) to all cells in the array so that they will all exhibit the same sensitivity. In this example the array is dimensioned to have the same pitch in both the row and column directions for good side lobe performance. The bridge-like interconnect structure 60 is preferably flexible and thus helps maintain the orientations of the cells of the array while permitting the array to be flexed and bent in a curved configuration for operation as a curved array transducer.

Figure 4:
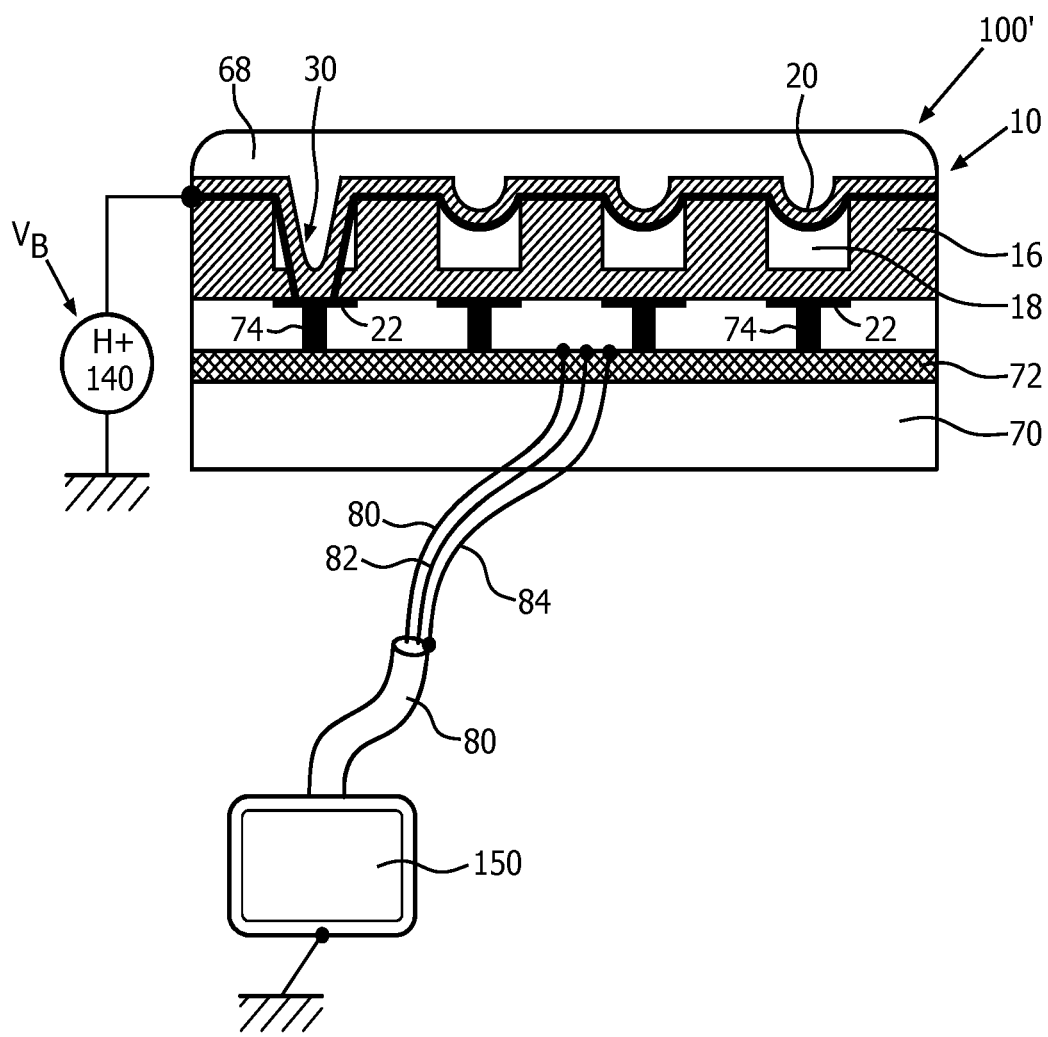
FIG. 4 is a cross-sectional view of an array of commonly biased CMUT cells illustrating the failure mode when one of the cells shorts out.

FIG. 4 illustrates a CMUT transducer probe 100' connected to an ultrasound system represented at 150 in the drawing. Shown in this illustration is an array of four CMUT cells 10 with a common top electrode 20 and individual bottom electrodes 22 for each CMUT cell. Dielectric 16 supports the top electrodes and membranes across the cavity 18 of each cell which allows the membranes and top electrodes to move in response to an applied DC bias voltage $V_B$ and received ultrasonic energy. In this embodiment a DC bias voltage H+ ($V_B$) is applied to the common electrode 20 to bias the top electrodes in the desired proximity with the floors of the cavities 18. A lens 68 or other covering protects the patient from direct contact with the high voltage of the DC bias. In accordance with a preferred implementation of the present invention the CMUT cells are fabricated on a substrate 70 of an ASIC of control integrated circuitry 72 for the CMUT cells. The bottom electrodes 22 of the CMUT cells are electrically connected to the circuitry of the ASIC by vias 74 through the top surface of the ASIC. Alternatively the CMUT can be formed on its own substrate 12 and connected to a separate ASIC through any of a number of techniques known to those skilled in the art such as flip chip connection, conductive adhesives, or through silicon vias. The ASIC circuitry of the ultrasound probe is connected to the ultrasound system 150 by a cable 80. The ultrasound system controls the transducer electronics of the ASIC through analog or digital control lines 82 and receives ultrasound signals through analog or digital signal lines 84.

FIG. 4 illustrates the problem addressed by the present invention, which is that the left-most CMUT cell has failed and its suspended top electrode 20 has collapsed to its bottom electrode 22 as shown at 30, shorting out the CMUT cell. Since the top electrodes of the cells are common, this failure also shorts out the top electrodes of all of the other interconnected cells. Not only are the cells now inoperative, but the coupling of the DC bias voltage directly to the via 74 applies current from the DC bias supply directly to the ASIC 72, potentially damaging the integrated circuitry of the ASIC.

Figure 5:
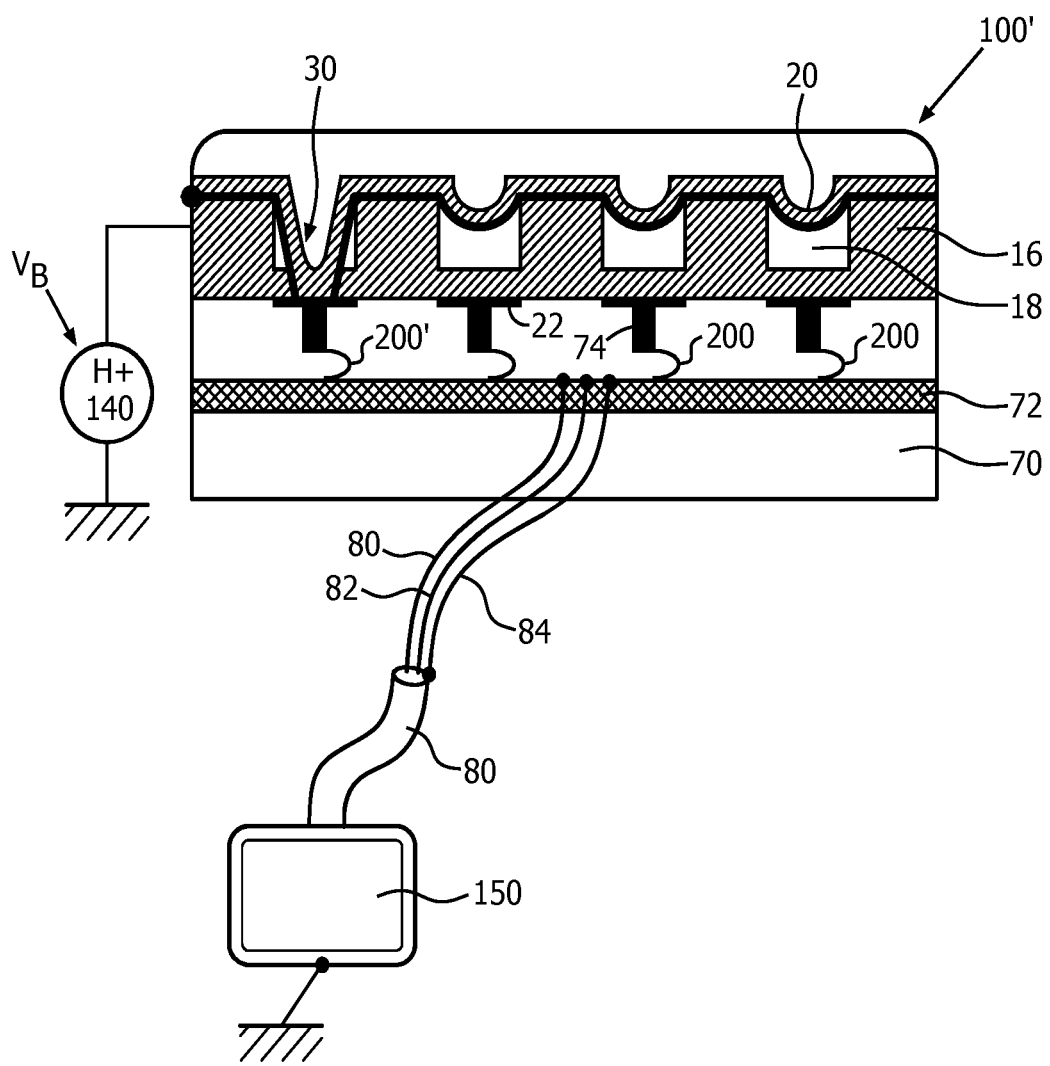
FIG. 5 is a cross-sectional view of a an array of commonly biased CMUT cells illustrating fuse protection of individual cells coupled for operating with a control ASIC in accordance with the principles of the present invention.

FIG. 5 illustrates the same CMUT probe 100' and ultrasound system 150 configuration but with fuse protection of individual CMUT cells in accordance with the present invention. Each MUT comprises a single fuse coupled to the bottom electrode, the fuse operating to open in the event of an overcurrent condition of the MUT cell to isolate the MUT cell from the other MUT cells of the array. It may be beneficial to have a fuse coupled to the signal electrode, which is coupled to the substrate. Often an overcurrent condition can cause a local redistribution of materials the fuse and electrode are made from. The closer the electrode and coupled to it fuse to the patient or acoustic window side, the higher is a risk of causing further shortages in the array due to the redistributed material with potential exposure of the patient to the bias voltage. In this embodiment individual fuses 200 are added in series with the bottom electrodes 22 of the cells to protect the electronics of the ASIC and to maintain the bias voltage to the other undamaged cells should one short out. In a preferred implementation of a CMUT cell of the present invention, the bottom electrode is not grounded but coupled to a DC reference potential and the a.c. drive signal for the cell (as well as received signals) are applied to and received at the bottom electrode. This way the bottom electrode of each cell has a function of the signal bearing electrode, while the top electrode (common electrode) of each cell can be grounded (coupled to the ground potential). This further improves patient safety of the array. In this case, the failure of the left-most cell as shown at 30 will cause fuse 200' to open, providing this protection by opening the shorted bias current path through the cell. The present invention provides a possibility to isolate a sensitive to high currents integrated circuitry (ASIC) from the failed CMUT cell in an elegant and compact design arrangement. Each CMUT cell requires only one fuse coupled to the signal electrode, wherein an activation of this fuse can cause an isilation of the corresponding CMUT cell from the signal line 84. The invention provides a reliable solution to the technical problem. In accordance with a further aspect of the present invention, the fuses are formed on the ASIC substrate 70. The present inventors have recognized that fuses occupy valuable area of the surface on which the CMUT cells are formed, thereby reducing the area available for acoustic generation and reception. Instead, the present inventors prefer to form the fuses in the ASIC substrate, taking advantage of the multiple layers within an ASIC to form fuses without limiting the acoustically active area of the probe. The fuses 200 can be fabricated of any of a metalized layer, a polysilicon layer, an active layer or in interconnections (vias) between layers of the ASIC chip. The fuses can be designed to operated by several known methods, including by thermal heating and by electro-migration. In a non-limiting example of FIG. 5 the top (common) electrodes of the CMUT cells are shown to be interconnected, therefore forming a continues electrode with the common voltage potential (either ground or reference bias).

Figure 6:
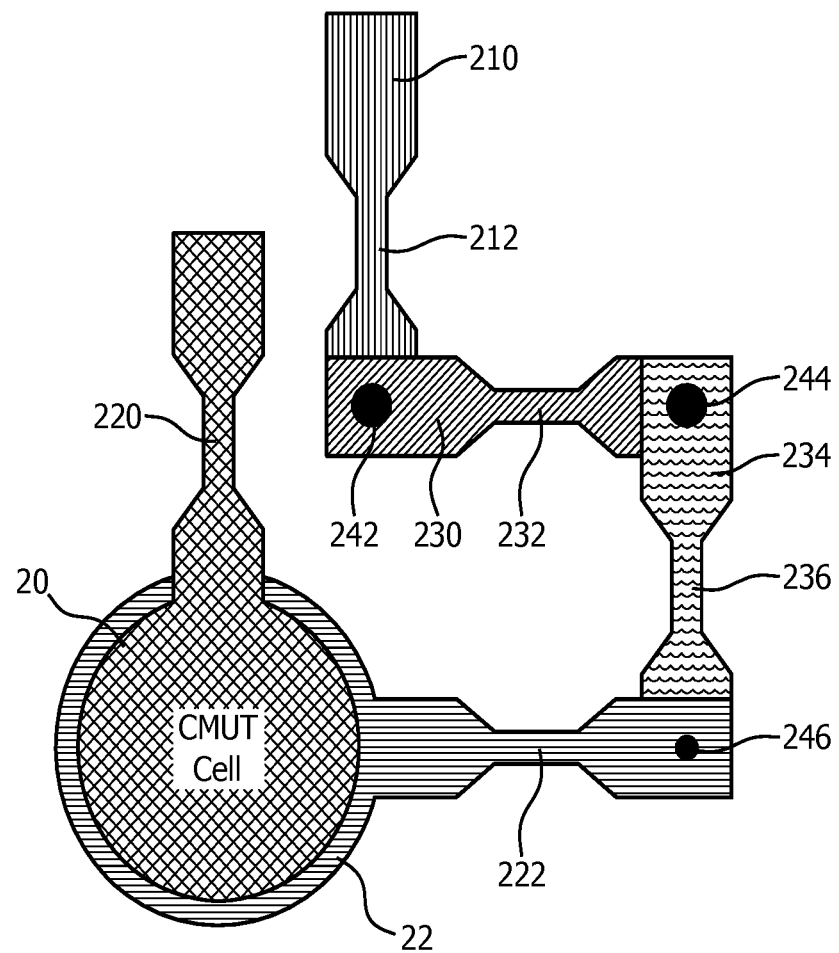
FIG. 6 illustrates semiconductor fabrication of a fuse for a CMUT cell in accordance with the principles of the present invention.

FIG. 6 illustrates in plan view several alternative techniques to implement a CMUT integrated circuit fuse in accordance with the principles of the present invention. These six illustrated techniques show how to make use of the multiple layers within an integrated circuit on which to deposit the various fuse segments shown. As the example shows, the various layers can be formed of various semiconductor materials. At the lower left of the drawing are the layers of a CMUT cell 10 including the top electrode 20 and the bottom electrode 22. One fuse technique is to narrow the conductive trace of the top electrode 20 as shown at 220. Another technique is to narrow the conductive trace of the bottom electrode 22 as shown at 222. This example also shows a polysilicon layer 210 and two integrated circuit metal layers 230 and 234 coupled in series with the bottom electrode 22. Electrical connections between layers are provided by conductive vias 242, 244, and 246. A fuse segment is shown formed in the polysilicon layer 210 by the narrowing of the layer at 212. Fuse segments are also shown formed in the integrated circuit metal layers 230 and 234 by the narrowing of the layers at 232 and 236. This example also shows a fuse formed by the small diameter of the via 246. The narrowing of the traces and the smaller via diameter each forces excessive electrical currents to flow in a narrow channel, causing either heat that opens the channel, or an opening of the channel through electro-migration, thereby opening the electrical path of DC bias current. A short circuited CMUT cell is thereby individually isolated from others still operating on the CMUT substrate and in the probe.

Figure 7:
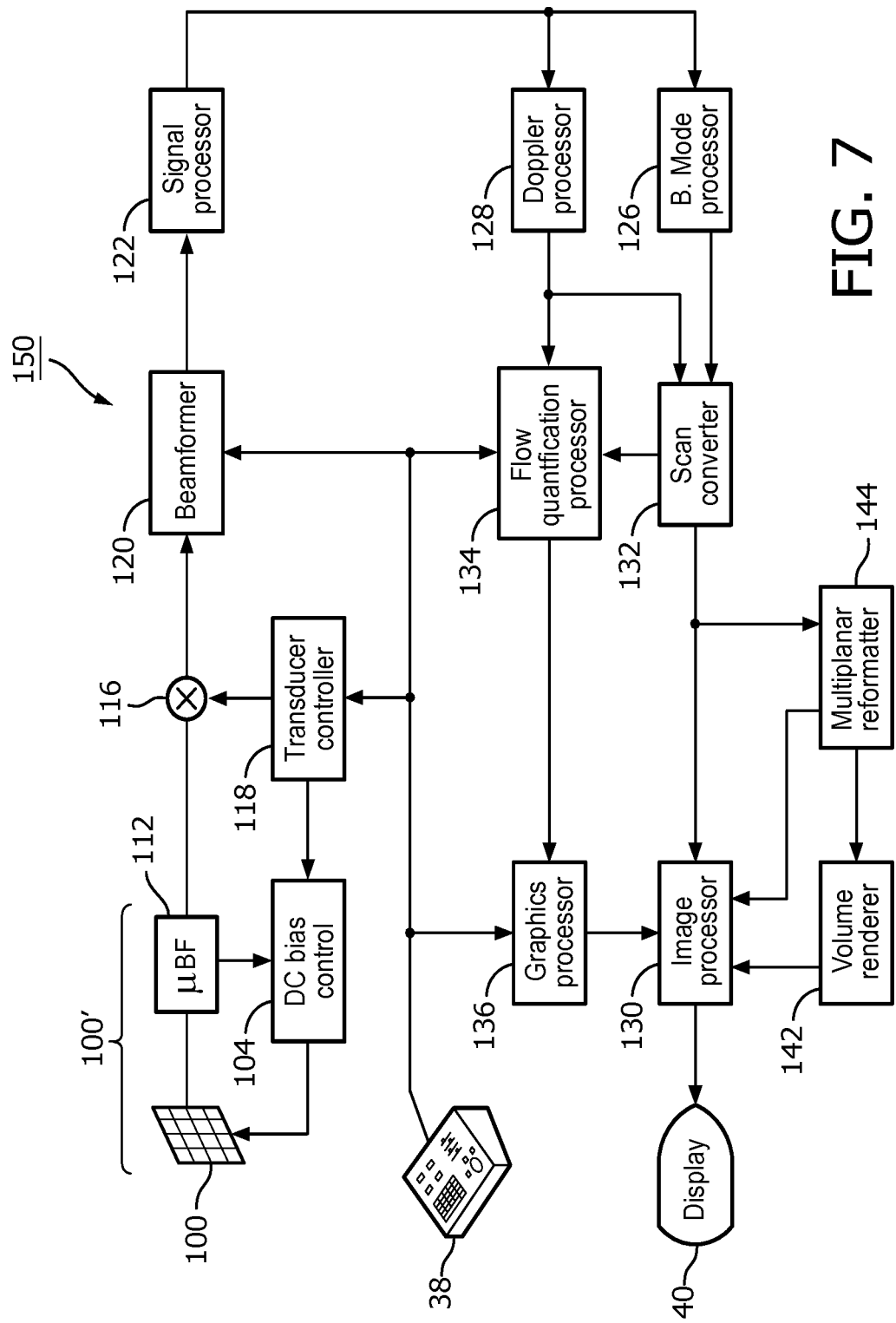
FIG. 7 is a block diagram of an ultrasonic imaging system suitable for use with a fuse-protected CMUT cell array of the present invention.

FIG. 7 illustrates in block diagram form an ultrasonic diagnostic imaging system 150 suitable for use with a MUT array probe of the present invention. A CMUT array 100 is located on the tip of a catheter or distal end of an ultrasound probe 100', together with a microbeamformer ASIC 112. The CMUT array 100 can be a one- or a two-dimensional array of MUT transducer elements capable of scanning in a 2D plane or in three dimensions for 3D imaging. The microbeamformer ASIC 112 (which also includes the control circuitry 72) controls the transmission and reception of signals by the CMUT array cells and also houses the fuses 200 for the CMUT cells as described above. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled to transmit/receive (T/R) switches 116 which switch between transmission and reception and protect the main system beamformer 120 from high energy transmit signals when a microbeamformer is not used and a transducer array is operated directly by the main system beamformer. The transmission of ultrasonic beams from the CMUT transducer array 100 under control of the microbeamformer ASIC 112 is directed by a transducer controller 118 coupled to the T/R switch and the main system beamformer 120, which receives input from the user's operation of the user interface or control panel 38. One of the functions controlled by the transducer controller is the direction in which beams are steered. Beams may be steered straight ahead from (orthogonal to) the transducer array, or at different angles for a wider field of view. The transducer controller 118 also controls a circuit 104 for the DC bias applied from the DC bias supply 140 to the CMUT cells which biases the cell membranes 14 to a partially or fully collapsed state for operation of the CMUTs in the desired mode of operation.

The partially beamformed signals produced by the microbeamformer 112 on receive are coupled to a main beamformer 120 where partially beamformed signals from individual patches of transducer elements are combined into a fully beamformed signal. For example, the main beamformer 120 may have 128 channels, each of which receives a partially beamformed signal from a patch of dozens or hundreds of CMUT transducer cells. In this way the signals received by thousands of transducer elements of a CMUT transducer array can contribute efficiently to a single beamformed signal. In a basic implementation the acoustic signals received from rows of CMUT cells are processed into beams from an image plane in front of the rows of cells to form a scanned 2D image.

The beamformed signals are coupled to a signal processor 122. The signal processor 122 can process the received echo signals in various ways, such as bandpass filtering, decimation, I and Q component separation, and harmonic signal separation which acts to separate linear and nonlinear signals so as to enable the identification of nonlinear echo signals returned from tissue and microbubbles. The signal processor may also perform additional signal enhancement such as speckle reduction, signal compounding, and noise elimination. The bandpass filter in the signal processor can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B mode processor 126 and a Doppler processor 128. The B mode processor 126 employs amplitude detection for the imaging of structures in the body such as the tissue of organs and vessels in the body. B mode images of structure of the body may be formed in either the harmonic mode or the fundamental mode or a combination of both as described in U.S. Pat. No. 6,283,919 (Roundhill et al.) and U.S. Pat. No. 6,458,083 (Jago et al.) The Doppler processor 128 processes temporally distinct signals from tissue movement and blood flow for the detection of the motion of substances such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors are coupled to a scan converter 132 and a multiplanar reformatter 144. The scan converter arranges the echo signals in the spatial relationship from which they were received into a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field corresponding with their Doppler-estimated velocities to produce a color Doppler image which depicts the motion of tissue and blood flow in the image field. The multiplanar reformatter will convert echoes which are received from points in a common plane in a volumetric region of the body into an ultrasonic image of that plane, as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.) The 2D or 3D images are coupled from the scan converter 32, multiplanar reformatter 44, and volume renderer 142 to an image processor 130 for further enhancement, buffering and temporary storage for display on an image display 40. In addition to being used for imaging, the blood flow velocity values produced by the Doppler processor 128 are coupled to a flow quantification processor 134. The flow quantification processor produces measure of different flow conditions such as the volume rate of blood flow. The flow quantification processor may receive input from the user control panel 38, such as the point in the anatomy of an image where a measurement is to be made. Output data from the flow quantification processor is coupled to a graphics processor 136 for the reproduction of measurement values with the image on the display 40. The graphics processor 136 can also generate graphic overlays for display with the ultrasound images. These graphic overlays can contain standard identifying information such as patient name, date and time of the image, imaging parameters, and the like. For these purposes the graphics processor receives input from the user interface 38, such as a typed patient name. The user interface is also coupled to the transducer controller 118 to control the generation of ultrasound signals from the transducer array 100 and hence the images produced by the transducer array and the ultrasound system. The user interface is also coupled to the multiplanar reformatter 144 for selection and control of a display of multiple multiplanar reformatted (MPR) images which may be used to perform quantified measures in the image field of the MPR images.

The invention claimed is:

1. A micromachined ultrasonic transducer (MUT) array which is protected from an overcurrent condition comprising:
a substrate;
a plurality of MUT cells formed on the substrate, each cell having a membrane comprising a top electrode and a bottom electrode coupled to the substrate,
wherein the plurality of MUT cells comprises a single, common electrode arranged to be coupled to a common reference potential and a plurality of signal electrodes arranged to individually be coupled to an a.c. drive signal, wherein the common electrode comprises the top electrodes of the plurality of MUT cells and each of the plurality of signal electrodes comprises a respective one of the bottom electrodes of the plurality of MUT cells; and
wherein each MUT cell further comprises one fuse coupled to a respective signal electrode of the plurality of signal electrodes, wherein the fuse is arranged to open in an event of an overcurrent condition of the MUT cell from the a.c. drive signal to isolate the MUT cell from the other MUT cells of the array.

2. The micromachined ultrasonic transducer (MUT) array of claim 1, wherein each fuse is coupled in series with the bottom electrode of a MUT cell.

3. The micromachined ultrasonic transducer (MUT) array of claim 1, wherein each fuse further comprises a fuse, which is arranged to open through heating or electromigration.

4. The micromachined ultrasonic transducer (MUT) array of claim 1, further comprising:
an integrated circuit coupled to the MUT array to control operation of the MUT cells,
wherein the fuses are located on the integrated circuit.

5. The micromachined ultrasonic transducer (MUT) array of claim 4, wherein the integrated circuit further comprises an application specific integrated circuit (ASIC).

6. The micromachined ultrasonic transducer (MUT) array of claim 5, wherein the ASIC further comprises a substrate, separate from the MUT substrate, with the integrated circuit formed on the substrate,
wherein the integrated circuit is electrically coupled to the MUT cells to control operation of the MUT cells.

7. The micromachined ultrasonic transducer (MUT) array of claim 6, wherein integrated circuit and its substrate are bonded to the MUT substrate.

8. The micromachined ultrasonic transducer (MUT) array of claim 6, wherein the ASIC further comprises a microbeamformer.

9. The micromachined ultrasonic transducer (MUT) array of claim 5, wherein the ASIC further comprises integrated circuitry, formed on the MUT substrate, the integrated circuitry electrically coupled to the MUT array to control operation of the array.

10. The micromachined ultrasonic transducer (MUT) array of claim 9, wherein the fuses are formed on the substrate with the integrated circuitry.

11. The micromachined ultrasonic transducer (MUT) array of claim 10, wherein the fuses are further formed on the substrate with the integrated circuitry with semiconductor materials.

12. The micromachined ultrasonic transducer (MUT) array of claim 11, wherein the semiconductor materials further comprises an integrated circuit metal layer or a polysilicon layer.

13. The micromachined ultrasonic transducer (MUT) array of claim 12, wherein the fuses further comprise narrowed traces of semiconductor material.

14. The micromachined ultrasonic transducer (MUT) array of claim 11, wherein the fuses further comprise vias of a predetermined dimension.

15. The micromachined ultrasonic transducer (MUT) array of claim 9, wherein the ASIC further comprises a microbeamformer.

16. The micromachined ultrasonic transducer (MUT) array of claim 1, wherein the top electrodes of the plurality of MUT cell are interconnected.

17. The micromachined ultrasonic transducer (MUT) array of claim 16, wherein the common reference potential comprises a ground potential, and wherein the plurality of signal electrodes is arranged to be coupled to both a D.C. reference potential and the a.c. drive signal.

* * * * *